United States Patent [19]

McDaniel, Jr. et al.

[11] Patent Number: 4,721,780
[45] Date of Patent: Jan. 26, 1988

[54] GLYCOSIDE PREPARATION DIRECTLY FROM AQUEOUS SACCHARIDE SOLUTIONS OR SYRUPS

[75] Inventors: Robert S. McDaniel, Jr.; Donald L. Johnson, both of Decatur, Ill.

[73] Assignee: A. E. Staley Manufacturing Company, Decatur, Ill.

[21] Appl. No.: 698,717

[22] Filed: Feb. 6, 1985

[51] Int. Cl.[4] .................... C07H 15/04; C07H 15/00; C07H 17/00
[52] U.S. Cl. .................... 536/18.6; 536/4.1; 536/120
[58] Field of Search .................... 536/4.1, 18.6, 120

[56] References Cited

U.S. PATENT DOCUMENTS

| | | | |
|---|---|---|---|
| 2,390,507 | 12/1945 | Cantor | 536/4.1 |
| 3,375,243 | 3/1968 | Nevin et al. | 536/18.6 |
| 3,565,885 | 2/1971 | Molotsky et al. | 536/18.6 |
| 3,928,318 | 12/1975 | Panusch et al. | 536/18.6 |
| 4,223,129 | 9/1980 | Roth et al. | 536/18.6 |
| 4,329,449 | 5/1982 | Roth et al. | 536/18.6 |

*Primary Examiner*—Ronald W. Griffin
*Attorney, Agent, or Firm*—Michael F. Campbell; James B. Guffey; J. Daniel Wood

[57] ABSTRACT

Glycoside products are successfully prepared directly from aqueous saccharide solutions or syrups, and with acceptably low levels of undesired higher polysaccharide by-products, by dissolving same in the desired alcohol reactant and contacting the resulting homogeneous aqueous saccharide+alcohol solution with an acid catalyst material in a fashion such that substantially no separate or distinct, predominantly aqueous saccharide solution phase is permitted to come into contact with said acid catalyst material under conditions conducive to homopolymerization of said saccharide reactant.

19 Claims, 6 Drawing Figures

GLYCOSIDE PREPARATION DIRECTLY FROM AQUEOUS SACCHARIDE SOLUTIONS OR SYRUPS

BACKGROUND OF THE INVENTION

The present invention pertains generally to the preparation of glycoside products by the acid catalyzed reaction of an alcohol reactant and a saccharide reactant. More particularly, such invention relates to a process for the preparation of such glycoside products directly from an aqueous solution or syrup of said saccharide reactant without having to first convert said saccharide reactant to substantially dry anhydrous or crystalline form.

Alkyl glycoside products such as, for example methyl glycoside, ethyl glycoside, propyl glycoside, butyl glycoside, etc, and their alkyl polyglycoside counterparts are generally known as is the preparation thereof via the reaction of an alcohol reactant and a saccharide reactant in the presence of a suitable acidic catalyst. See in this regard U.S. Pat. No. 2,390,507 to Cantor (issued Dec. 11, 1945); U.S. Pat. No. 3,219,656 to Boettner (issued Nov. 23, 1965); U.S. Pat. No. 3,450,690 to Gibbons et al. (issued June 17, 1969) and U.S. Pat. No. 3,974,138 to Lew (issued Aug. 10, 1976).

Also known is the fact that lower alkyl glycosides such as methyl, ethyl, propyl, butyl, etc. glucosides are useful as intermediates for the preparation of longer chain (e.g., higher alkyl) glycoside products which in turn gave surface active characteristics and are useful in a variety of surfactant, emulsifier, detergent, etc. end-use applications.

In the manufacture of water soluble alkyl glycoside products from water-soluble monosaccharide and polysaccharide starting materials (such as glucose, maltose, sucrose, xylose, lactose, and the like) by the acid catalyzed reaction thereof with an alcohol reactant (such as, for example, propanol, butanol, amyl alcohol, 2-ethylhexyl alcohol, octyl alcohol, etc.), it has generally been the practice to introduce the saccharide reactant into the reaction mixture in substantially dry (e.g., anhydrous or hydrated crystalline) form and to conduct said reaction under substantially anhydrous conditions so as to avoid the formation of substantial quantities of undesired insoluble higher polysaccharide reaction by-products.

Crystalline dextrose is relatively expensive as a potential starting point saccharide raw material. Similarly, the inclusion of a special step in the overall reaction process for the preliminary conversion of an aqueous saccharide solution of syrup feed stream into substantially dry, anhydrous or crystalline form prior to the use thereof in the desired saccharide/alcohol reaction entails or introduces added complication and expense to the overall glycoside manufacturing process. Accordingly, it would be highly desirable to provide a process whereby an aqueous saccharide solution or syrup could be directly reacted with an alcohol reactant (i.e. without the special need for conducting said reaction under substantially anhydrous conditions) while at the same time avoiding the generation of substantial quantities of undesired insoluble higher polysaccharide by-product materials.

SUMMARY OF THE INVENTION

It has now been discovered that glycoside products may be prepared by the direct, acid catalyzed reaction of an aqueous saccharide solution or syrup with an alcohol reactant (and without the generation of substantial quantities of undesired polysaccharide by-products) by conducting said reaction in a fashion which prevents any distinct, predominantly aqueous saccharide solution or syrup phase from coming into contact with the acid catalyst during said reaction under conditions conducive to homopolymerization of said saccharide reactant within said distinct aqueous solution or syrup phase. Accordingly, the present invention in one of its broader respects is a process for preparing a glycoside product by reacting a saccharide reactant with an alcohol reactant which process comprises:

a. admixing an aqueous solution of the saccharide reactant with the alcohol reactant to provide a homogeneous aqueous reaction phase comprising said saccharide and alcohol reactants and water;

b. reacting said saccharide reactant with said alcohol reactant by contacting said homogeneous aqueous reaction phase with an acid catalyst; and c. conducting steps (a) and (b) above in a fashion which prevents any distinct, predominantly aqueous saccharide solution or syrup phase from coming into contact with the aforementioned acid catalyst under conditions conducive to homopolymerization of said saccharide reactant.

The present invention is particularly advantageous in the sense it permits the preparation of alkyl glycoside products directly from an aqueous saccharide solution feed stream and thereby eliminates the need for acquiring or providing a substantially dry, anhydrous or crystalline saccharide product as the necessary raw material or starting point reactant for the glycoside manufacturing process of interest.

BRIEF DESCRIPTION OF THE DRAWINGS

In FIGS. 1-4, the various binary alcohol+aqueous dextrose syrup or ternary (i.e., alcohol+aqueous dextrose syrup+alkyl glucoside) compositions falling within or encompassed by the designated "single-phase region" represent compositions which form homogeneous single phase solutions comprising the alcohol, dextrose, water and, when present, alkyl glucoside product and which are suitably contacts with acid catalyst in accordance with the process of the present invention. Compositions falling within the designated "two phase region" of the figures are illustrative of those which separate into two distinct phases (i.e. a separate, predominantly aqueous syrup phase and the desired homogeneous reaction phase comprising aqueous dextrose syrup dissolved in the alcohol reactant) and which are prevented from contacting the acid catalyst under conditions conducive to dextrose homopolymerization in accordance with the present invention. The phase diagrams depicted in FIGS. 1-4 are representative of the systems indicated over a temperature range of from about 110° to about 150° C.

The phase diagrams depicted in the various Figures were generated by admixing known proportions of the indicated dextrose syrup with known quantities of the specified alcohol and of the corresponding alkyl glucoside product in a glass pressure bottle and agitating same in an oil bath maintained at the temperature of interest. The contents of the bottle were visually inspected at 15 minute intervals. Compositions appearing homogeneous and clear upon visual inspection were classified as being "single phase". Compositions remaining heterogeneous after an hour of agitation at the test temperature were characterized as "two phase" systems. In FIGS. 1-4 and 6, the phase diagram data was generated at a temperature in the range of 110°-150° C. and no significant difference in solubility or phase separation characteristics was detected over that particular temperature range. The FIG. 5 phases diagram was generated at 40° C.

The phase diagrams depicted in FIGS. 1-4 are "partial" in the sense that those portions of the phase diagrams relating to compositions containing greater than 35 weight percent alkyl glucoside product and compositions containing greater than 35 weight percent dextrose syrup are not presented. Limitation of the phase diagrams to the compositional area indicated was for the sake of convenience only and was intended to focus primarily upon those compositions having syrup, alcohol and alkyl glucoside proportions which would generally be considered to represent the most advantageous or desirable regions in which to operate from a practical economic perspective. Completion or development of said phase diagrams for component proportions outside the ranges illustrated (or for alcohol reactants, alkyl glycoside products and/or aqueous saccharide solutions different from those illustrated) would plainly be well within capabilities of the normally skilled artisan and may be conveniently conducted in accordance with the procedure set forth above in facilitating the broad applicability and practice of the presently disclosed invention.

Figure 1:
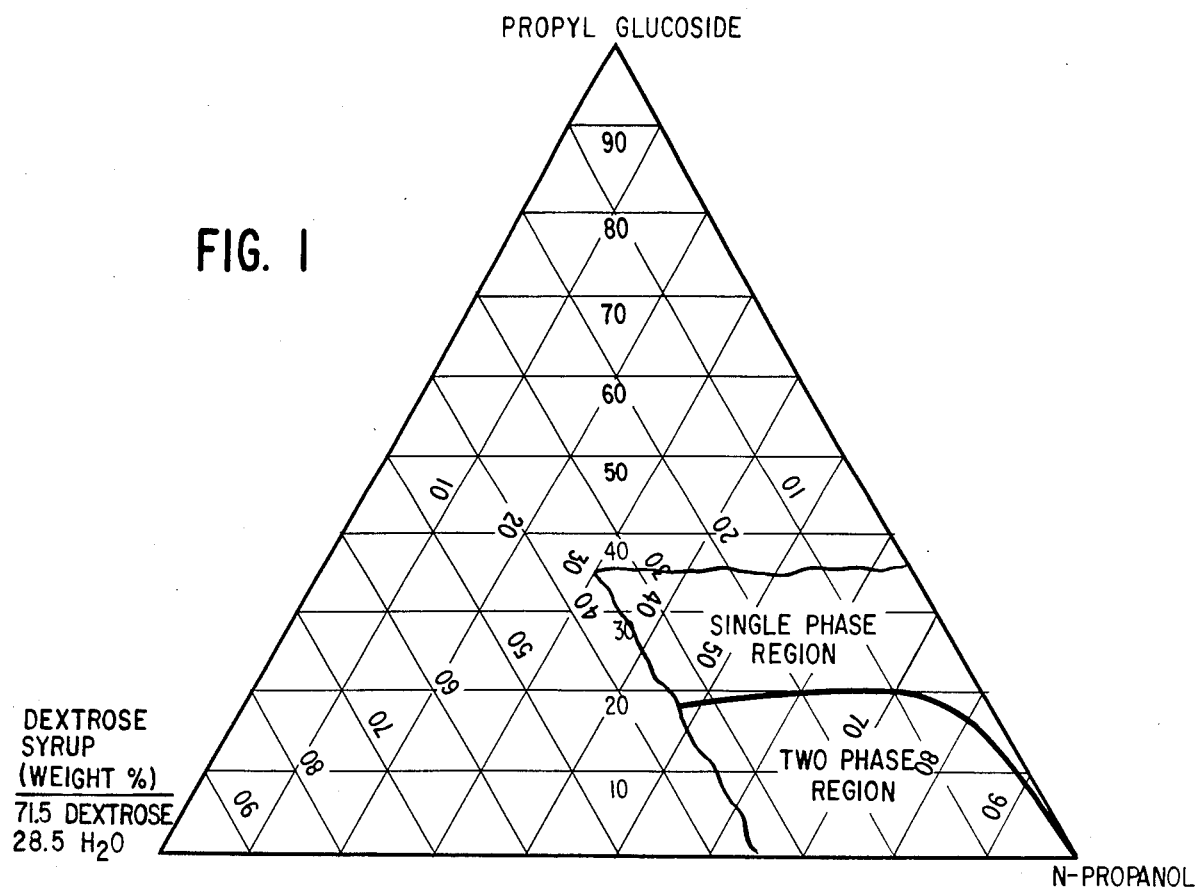
FIG. 1 is a partial triangular graph or phase diagram depicting the boundary line between the homogeneous single phase-forming region and the heterogeneous or two phase-forming region for certain compositions composed of various proportions of n-propanol, propyl glucoside and an aqueous dextrose syrup containing approximately 71.5 weight percent dissolved dextrose solids and about 28.5 weight percent water on a total syrup weight basis.
Figure 2:
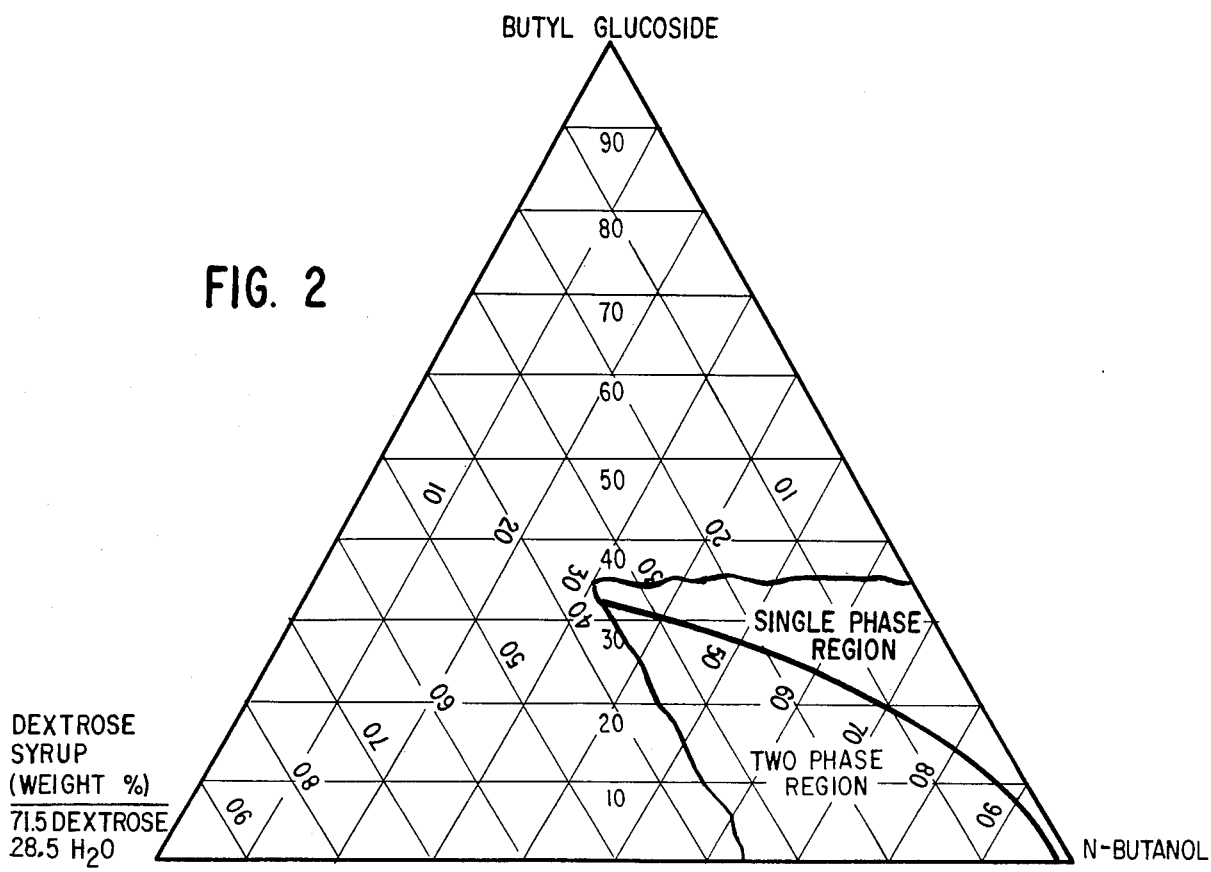
FIG. 2 is a similar partial triangular phase diagram for compositions composed of n-butanol, butyl glucoside and the same aqueous dextrose syrup.
Figure 3:
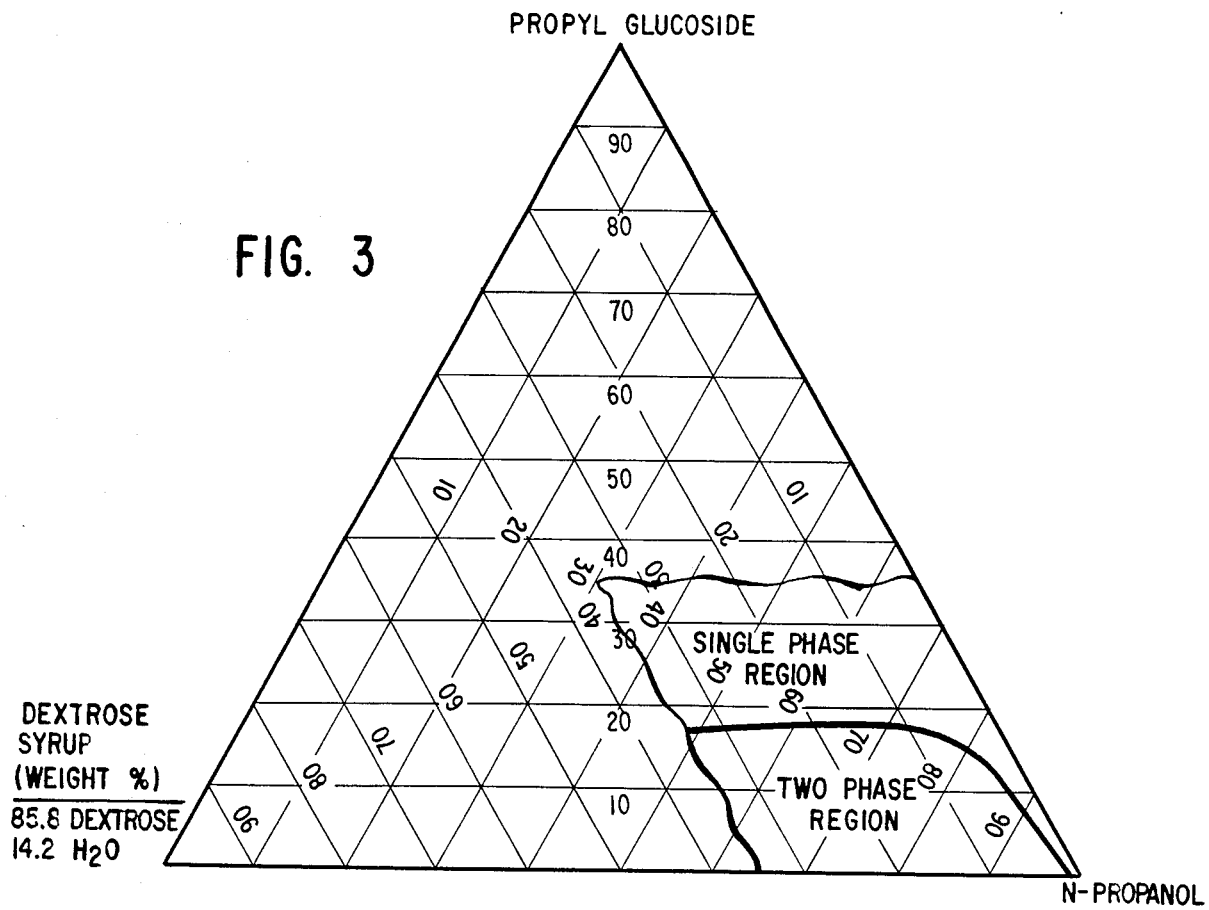
FIG. 3 is a partial triangular phase diagram for n-propanol/propyl glucoside/aqueous dextrose syrup compositions similar to those in FIG. 1 except that the aqueous dextrose syrup employed comprises 85.8 weight percent of dissolved dextrose solids and 14.2 weight percent water.
Figure 4:
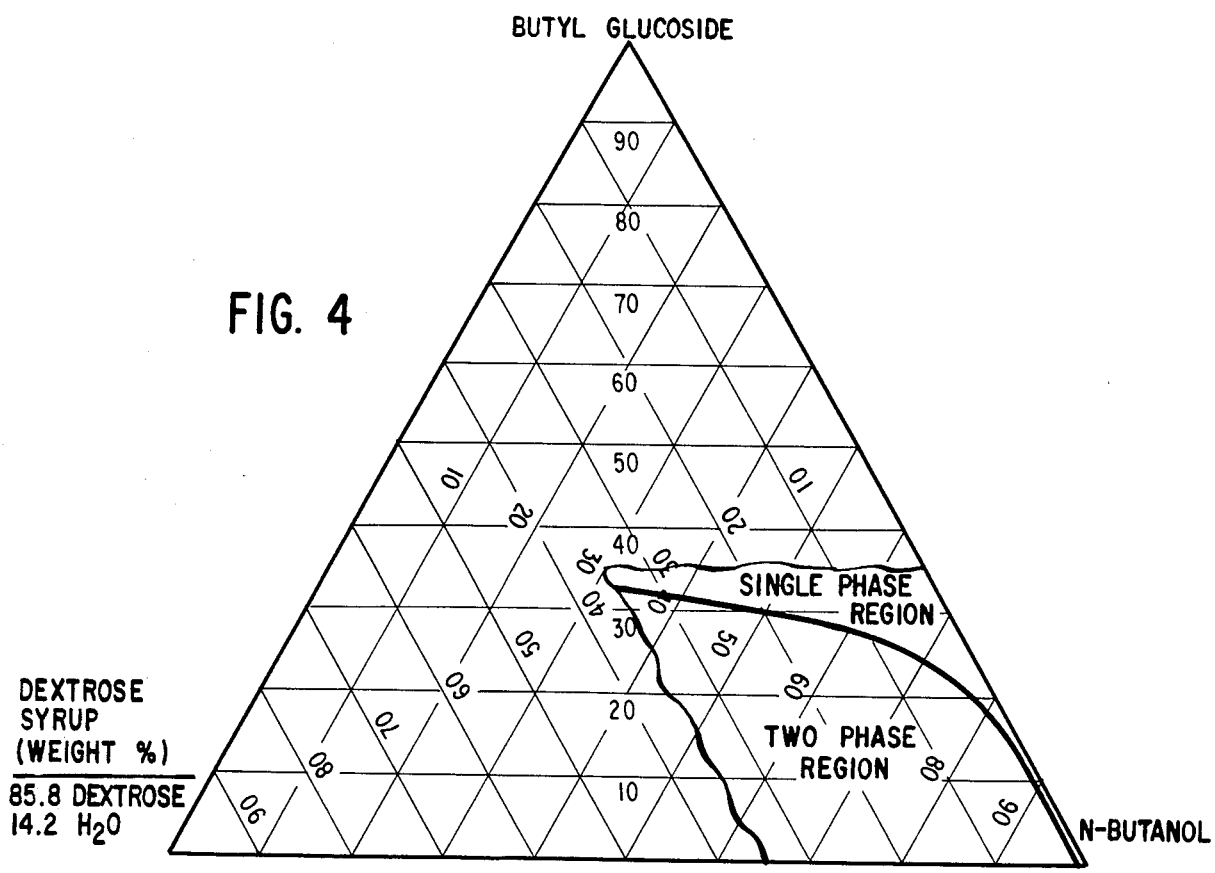
FIG. 4 is a partial triangular phase diagram for n-butanol/butyl glucoside/aqueous dextrose syrup compositions similar to those of FIG. 2 except that the aqueous dextrose syrup employed therein is composed of 85.8 weight percent dextrose and 14.2 weight percent water.
Figures 5, 6:
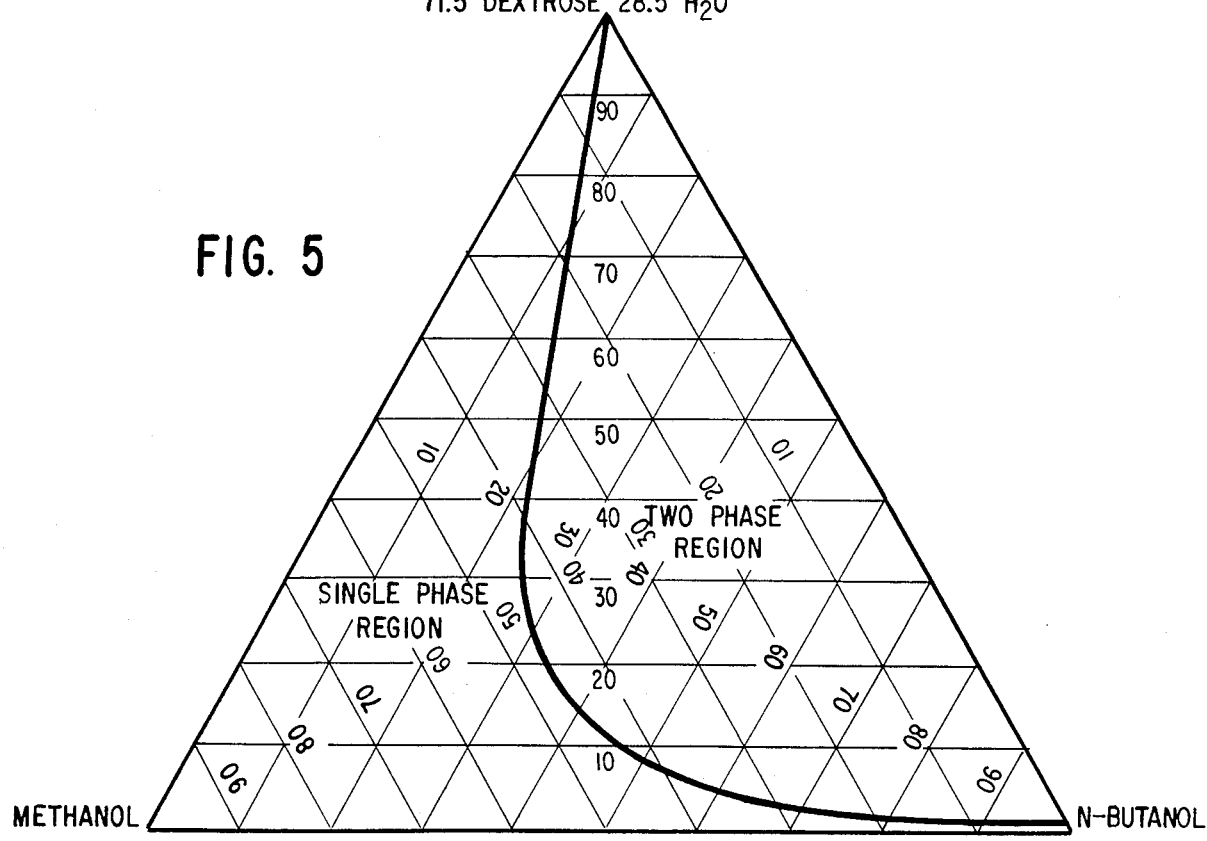

FIG. 5 is illustrative of a hereinafter more fully discussed special or preferred aspect of the present invention in which the compatibility as between an aqueous saccharide solution and a relatively hydrophobic alcohol (e.g. n-butanol) can be substantially improved by the inclusion of methanol within a mixture of same.

FIG. 6 illustrates that selection of a methanol/butanol/dextrose syrup composition within the single phase region of FIG. 5 prevents phase separation during the course of the desired alkyl glucoside preparation process by substantially enlarging the single phase region. (Compare in this regard FIG. 2 with FIG. 6).

DETAILED DESCRIPTION OF THE INVENTION

Saccharide materials to which the present invention is applicable include water soluble mono-saccharide materials such as, for example glucose, galactose, mannose, xylose, arabinose, fructose, etc. as well as water soluble polysaccharide material such as sucrose, maltose, maltotriose, lactose, xylobiose, mellibiose, cellobiose, raffinose, stachiose, and the like and various mixtures of said mono- and polysaccharide materials. Such saccharide reactants are introduced into the reaction process of the present invention in the form of aqueous saccharide solutions or syrups, typically comprising from about 20 to about 90 ( most preferably from about 50 to about 80) weight percent of saccharide (e.g., glucose, etc.) solids, and from about 10 to about 80 (preferably from about 20 to about 50) weight percent water, on a total aqueous saccharide solution weight basis.

Alcohols suitable for reaction with the aforementioned saccharide materials in accordance with the present invention include monohydric saturated aliphatic alcohols (preferably those having from 1 to about 8 carbon atoms such as, for example, methanol, ethanol, n-propanol, isopropanol, n-butanol, amyl alcohol, 2-ethylhexyl alcohol, octyl alcohol, etc) so as to provide the corresponding alkyl glycoside reaction products (preferably $C_1$ to about $C_8$ alkyl glycosides) as well as polyhydric saturated aliphatic alcohols (such as, for example, ethylene glycol, propylene glycol, butylene glycol, glycerol and the like) so as to provide hydroxylalkyl glycoside reaction products. Suitable alcohol reactants also include unsaturated aliphatic alcohols and aromatic alcohols such as allyl alcohol, 2-ethylhexenyl alcohol and benzyl alcohol as well as alkyl phenols and their alkoxylated derivatives. As used herein, the term "glycoside" is employed to connote glycoside products wherein the alcohol-derived substituent of concern can either be saturated aliphatic, unsaturated apiphatic or aromatic in character.

The benefits and advantages of the present invention are most pronounced in the case of alcohol reactants in which water and/or aqueous solutions of the saccharide reactant of interest has limited solubility or miscibility. Alcohol reactants for which the present invention is particularly applicable and beneficial include $C_2$ to $C_6$ (especially $C_2$ to $C_4$) monohydric saturated and unsaturated aliphatic alcohols (e.g., $C_2$ to $C_6$, especially $C_2$ to $C_4$, alkanols such as ethanol, n-propanol, isopropanol, n-butanol, pentanol and hexanol) and especially the relatively more hydrophobic species thereof such as, for example, isopropanol, n-propanol, n-butanol, allyl alcohol and the like.

A key feature of the present invention resides in conducting the acid catalyzed alcohol/saccharide reaction of interest in a fashion such that a persistent, distinct, predominantly aqueous saccharide solution or syrup phase either is not formed during the course of the overall reaction process of interest or, if formed somewhere in the process, is not permitted to be in contact with the acid catalyst under conditions conducive to saccharide homopolymerization. As a practical matter, the propensity of a given aqueous saccharide reactant solution to form a separate and distinct, predominantly aqueous saccharide solution phase when admixed with (i.e., to phase separate within) a given alcohol reactant will vary as a function of the relative compatibility or miscibility of said aqueous saccharide solution with the particular alcohol reactant of concern. Generally speaking, said propensity is greater or more pronounced in the case of those alcohol reactants which are relatively more hydrophobic in character. In short, the more hydrophobic the alcohol reactant is, typically, the lower will be its saturation point relative to the aqueous saccharide solution with the result that phase separation so as to form a separate or distinct, predominantly aqueous saccharide solution phase and a separate ternary homogeneous saccharide+water+alcohol composition phase will occur at relatively lower water-(or aqueous saccharide solution)-to-alcohol ratios or proportions.

A number of alternative techniques may be suitably employed to avoid contact of a separate predominantly aqueous saccharide solution phase with the acid catalyst under the reaction conditions of interest and to thereby avoid the undesired formation of high molecular weight, unsubstituted polysaccharide reaction by-products. Generally speaking, however, each of the various alternatives typically utilize or employ an excess of the alcohol reactant (i.e. at least at that stage of the process in which the reaction mixture of interest is concurrently exposed to the acid catalyst employed and to reaction conditions conducive to reaction of the alcohol reactant with the saccharide reactant) so as to ensure that the resulting reaction mixture does not exceed (i.e., is at or below) the saturation point (i.e., phase separation level) of the aqueous saccharide solution within the desired aqueous alcohol/saccharide reaction mixture. This will typically also constitute a substantial stoichiometric excess of the alcohol reactant over that required for the desired degree of reaction with, or substitution of, the saccharide reactant of concern.

With regard to the foregoing, it has been observed that the compatibility or miscibility as between the aqueous saccharide solution and certain alcohol reactants (for example, those alcohols containing 2 or more carbon atoms and especially in the case of those alcohols containing 3 or 4 carbon atoms or more) can be notably improved by the inclusion of at least a small quantity (e.g., from about 5 to about 80 weight percent on a total reaction mixture weight basis) of methanol within the aqueous saccharide/alcohol reaction mixture. Accordingly, it is oftentimes advantageous and preferable in those instances wherein the desired alcohol reactant contains 2 or more (especially from 3 to 8) carbon atoms to include at least a small quantity (preferably from about 25 to about 80, most preferably from about 50 to about 80, weight percent on a total reaction mixture weight basis) of methanol within the aqueous alcohol/-saccharide reaction mixture so as to enhance the miscibility as between the aqueous saccharide solution and the somewhat more hydrophobic (e.g., $C_2$ or $C_3$ or more) alcohol reactant of interest. Naturally, when the foregoing technique is employed, the initially resulting glycoside product will tend to be a mixture of methyl glycoside and a higher (e.g., $C_2$ or more) alkyl, alkenyl or aryl glycoside derived from the corresponding higher alcohol reactant employed. In such instance, said mixture may constitute (and be recovered and employed as) the desired reaction product. Alternatively, said initially resulting glycoside product mixture can be converted (e.g., in-situ) predominantly to the higher alkyl, alkenyl or aryl glycoside product by continuing the acid catalyzed reaction in the process of excess, unreacted higher alcohol reactant (e.g. gradually adding additional quantities of same as necessary or desired) while removing methanol from the reaction mixture. In this latter instance, of course, the later stage of the overall reaction process essentially constitutes a methanol/higher alcohol interchange reaction wherein initially produced methyl glycoside in converted to the desired higher alkyl, alkenyl or aryl glycoside product with the attendant regeneration of methanol which can then be suitably removed from the reaction mixture via distillation or other convenient methanol separation techniques.

In practicing the process of the present invention, it is not essential that phase separation as between a separate, predominantly aqueous saccharide solution phase and the desired homogeneous aqueous alcohol/saccharide reaction mixture phase (or the existence of a separate, predominantly aqueous saccharide solution phase) be avoided at all times throughout each and every step or facet of the overall process or operation so long as the existence of such a separate, predominantly aqueous saccharide solution phase is avoided concurrently with a combination of (a) the presence of the requisite acid catalyst and (b) reaction conditions (e.g., temperatures, pressures, etc.) conducive to the undesired polymerization of said saccharide reactant with itself.

Thus, for example, as an initial step for preparing the desired single phase homogeneous aqueous alcohol/saccharide reaction mixture (i.e. wherein the alcohol reactants is partially or fully saturated with the aqueous saccharide solution of interest) in advance of the actual acid catalyzed reaction step itself, it may be desirable and advantageous (particularly in the context of a continuous or semi-continuous overall reaction process or operation) to form said homogeneous reaction mixture by means of a 2 phase (e.g. countercurrent) liquid-liquid mass transfer operation wherein an alcohol-continuous phase or flow stream (a) is contacted with (i.e., so as to at least partially saturate same with) an excess (or/less) of a discontinuous, dispersed aqueous saccharide solution and (b) is separated from any remaining excess or residual separate or distinct predominantly aqueous saccharide solution phase in advance of the actual subsequent or downstream acid catalyzed reaction step per se. In such event, the subsequent or downstream reaction step can suitably entail a separate step for heating the resulting reaction temperature followed by the contacting of same with the desired acid catalyst or the requisite heating step can be simultaneously conducted in conjunction with the acid catalyst contacting operation. Alternatively still, one or both of the aqueous saccharide solution and/or the alcohol reactant feed streams can be preheated sufficiently to facilitate the desired downstream reaction temperature in advance of both the aforementioned liquid-liquid contacting operation and the subsequent acid catalyst contacting operation.

In the context of the aforementioned type of continuous or semi-continuous reaction process, the choice of the particular type of acid catalyst for use in the actual reaction step of the process is not particularly critical. Thus, for example, said acid catalyst can suitably be (1) gaseous in character (and, for example, can be bubbled through, or absorbed or dissolved in, the homogeneous, single phase partially or fully aqueous saccharide solution-saturated alcohol reaction mixture of interest); (2) a liquid acid catalyst which can either be miscible or immiscible within the homogeneous aqueous alcohol/-saccharide reaction mixture of interest (and which can thus either be dissolved or dispersed in said reaction mixture of reaction catalysis purposes); or (3) a solid acid catalyst which can either be soluble or insoluble in said aqueous alcohol/saccharide reaction mixture and which, if insoluble, can either be dispersed within, or distributed throughout, said reaction mixture or can be employed in the form of a fixed or confined, packed catalyst bed through which said reaction mixture can be conveniently passed or which, if soluble, can be suitably dissolved within said reaction mixture.

In the case of a continuous or semi-continuous process such as that set forth above, the use of a particulate, insoluble solid acid catalyst in the reaction step of the process (and especially the use of a porous, particulate insoluble solid acid catalyst in the form of a fixed or confined, packed bed thereof) is particularly convenient and preferred.

The process of the present invention can, if desired, also be conveniently and suitably conducted on a batchwise basis within one or more stirred tanks or similar reaction vessels. The sequence of steps in such a batchwise operation can suitably be the same as that outlined above in the context of a continuous or semi-continuous process or operation; namely, (1) admixing the aqueous saccharide solution and the alcohol reactant thoroughly so as to form a partially or fully aqueous saccharide solution-saturated single phase homogeneous aqueous alcohol/saccharide reaction mixture; (2) separating any remaining non-dissolved predominantly aqueous saccharide solution phase from said reaction mixture; and thereafter (3) contacting said reaction mixture with an acid catalyst at the desired reaction temperature.

Insoluble particulate (preferably porous insoluble particulate) solid acid catalyst materials suitable for use herein include macroreticular acidic ion exchange resins (e.g., macroreticular sulfonic acid ion exchange resins, perfluorinated sulfonic acid resins, etc); and the like.

Suitable liquid form acid catalysts for use herein include strong mineral acids such as hydrochloric acid, sulfuric acid, nitric acid, phosphoric acid, hyrpohosphorous acid, etc.; strong organic acids such as paratoluene sulfonic acid, methane sulfonic acid; tri-fluoromethane sulfonic acid, dodecylbenzene sulfonic acid, etc.; and the like.

Suitable gaseous acid catalyst materials for use herein include gaseous HCl, boron trifluoride, and the like.

The temperature at which the above-discussed alcohol-saccharide reaction is conducted is not particularly critical but will usually be an elevated temperature relative to the normal ambient or room temperature of about 20°-25° C. Preferably said reaction will normally be conducted at a temperature of from about 60° to about 200° C. (and especially within the range of from about 80° to about 150° C.).

The actual reaction of the saccharide reactant and the alcohol reactant in accordance with the present invention is basically a condensation reaction in which a molecule of water is liberated or generated for each instance in which a molecule of alcohol reacts with a saccharide molecule. Since such reaction is reversible in character, it is typically desirable to remove water from the reaction mixture during the course of the reaction in order to shift the equilibrium in favor of the desired glycoside product and thereby drive the reaction toward completion. Additionally, such a water removal feature is also typically desirable in order to prevent accumulated water of condensation from causing an undesired phase separation (i.e. the formation of a separate and distinct predominantly aqueous saccharide solution phase) during the course of the subject reaction. This latter consideration is, of course, of special significance or importance in those instances wherein the single phase, homogeneous aqueous alcohol/saccharide reactant solution, as initially formed prior to the reaction step, is already at or relatively near to its saturation point.

In conducting the alcohol/saccharide reaction in accordance with the present invention, it is generally desirable to contact same at a pressure which facilitates water removal while at the same time maintaining the desired reaction temperature. Thus, for example, subatmospheric pressure (e.g., on the order of from about 1 to about 25 inches of mercury, about 3.39 to about 84.66 KPa, below normal atmospheric pressure) is generally preferred in the case of alcohol reactants containing 4 or more carbon atoms and atmospheric or super-atmospheric pressure (e.g., from about 1 to about 400 inches of mercury, about 3.39 to about 1,354.55 KPa, above normal atmospheric pressure) is typically preferred when $C_1$ or $C_2$ alcohols such as methanol or ethanol represent the alcohol reactant of concern. In the case of $C_3$ alcohols such as n-propanol, isopropanol and allyl alcohol, the alcohol/saccharide reaction of concern can conveniently be conducted at either atmospheric, subatmospheric or superatmospheric pressure, as desired, and depending generally upon the reaction temperature desired in a given instance. In some cases water may form an azeotropic mixture with the alcohol reactant employed and the indicated distillation step will thus remove both water and a portion of the alcohol reactant in the form of an alcohol/water azeotrope, In such event, it is usually desirable and preferable to gradually or intermittently add additional alcohol reactant to the reaction mixture during the course of said reaction in order to replace that portion thereof which leaves the reaction as a result of the indicated alcohol/water azeotropic distillation.

Following completion of the above-described alcohol-saccharide reaction, the resulting glycoside product can suitably be recovered from the reaction mixture in any convenient fashion such as, for example, precipitation or crystallization followed by either filtration or centrifugation; distillation or evaporation of excess alcohol reactant; liquid-liquid extraction; etc.

Alternatively, the acid catalyst can either be neutralized and/or removed from the reaction mixture, as appropriate, and the resulting glycoside/alcohol solution can be marketed, used or subjected to further processing operations in that form without further purification or product recovery treatments.

The present invention is further understood and illustrated by reference to the following examples thereof in which, unless otherwise indicated, all parts and percentages are on a weight basis, and all temperatures are stated in °C.

EXAMPLE 1

One liter of n-propanol and 50 grams of a macroreticular sulfonic acid ion exchange resin are charged to a 2 liter round bottom flask which is connected to a Buchler rotary evaporator and which is situated in a hot oil bath. The n-propanol/sulfonic acid resin mixture is heated to a temperature of about 107° to 109° C. and 200 grams of an aqueous dextrose syrup containing 50 weight percent dextrose solids and 50 weight percent water on a total syrup weight basis are gradually added over a period of 2 hours. During addition of said dextrose syrup, the reaction mixture is maintained under a vacuum of 5 inches of Hg (16.93 KPa) below atmospheric and a slow (about 60 cc/hr) propanol-water co-distallation is maintained. After approximately 250 cc of a propanol-water mixture has been removed via said co-distillation, syrup addition is interrupted and 250 cc of fresh propanol is slowly added to the reaction mixture over a 5 to 10 minute period so as to avoid a drastic reduction in the reaction temperature.

After all of the dextrose syrup has been added, visual examination of the flask shows no noticeable catalyst agglomeration and no material adhering to the walls or bottom of the flask.

The catalyst is then removed by filtration and the resulting filtrate is concentrated by vacuum distillation using the rotary evaporator (at about 90° C. and 27 inches Hg. 91.43 KPa, vacuum) to remove excess propanol until no further distillate is observed. Upon completion of said distillation, approximately 115.5 grams of residual material remains. Said material is predominantly the desired propyl glucoside reaction product and contains about 11.65 weight percent of unreacted dextrose on a dry substance weight basis.

EXAMPLE 2

An aqueous dextrose syrup containing about 128.5 grams of dextrose and about 129 grams of water is gradually added over a period of 1.25 hours to a mixture of 1000 ml of n-propanol and 62 grams of an acidic ion exchange resin contained within a reaction apparatus as described in Example 1 above. The reaction is conducted at 110° C. and at a vacuum of from 5 to 6 inches of Hg (16.93 to 20.32 KPa) below atmospheric pressure, with an a propanol-water mixture being co-distilled off during the course of same. When approximately 250 ml of a propanol-water mixture has distilled off, the syrup addition is interrupted and 250 ml of fresh propanol is added to the reaction mixture.

Following completion of the syrup addition, the reaction is permitted to continue for an additional period of 2 hours. At the end of said reaction period, the catalyst is removed by filtration. The resulting filtrate solution has a density of 0.85 g/cc and contains 26.4 weight percent solids on a total weight basis, of which greater than 70 weight percent (on a dry solids weight basis) is the desired propyl-monoglucoside product and 1.02 weight percent (on a dry solids weight basis) is unreacted dextrose starting material.

EXAMPLE 3

In this example, butyl glucoside is prepared by reaction of n-butanol with an aqueous dextrose syrup.

In conducting said reaction, a mixture containing 800 g n-butanol and 55 g of a macroreticular sulfonic acid ion exchange resin are charged to the reaction apparatus described in Example 1 above. The temperature is adjusted to about 112° C. and a vacuum of 12.5 inches of Hg (42.33 KPa) below atmospheric is applied. Thereafter 400 g of an aqueous dextrose syrup containing 50 weight percent dextrose on a total syrup weight basis is gradually added to the butanol/catalyst mixture over a 2.25 hour period. A butanol-water mixture is co-distilled off during the reaction process and 250 ml of make-up butanol is added to the reaction mixture at that point in the reaction process at which approximately that quantity of butanol has departed the reaction mixture via said co-distillation. The reaction is continued for an additional period of one hour following completion of the dextrose syrup addition.

Following removal of the ion exchange resin catalyst by filtration, the resulting reaction mixture is found to be an n-butanol solution containing 31.7 weight percent solids (on a total solution weight basis) of which greater than 70 weight percent (dry solids weight basis) is the desired butyl monoglucoside product. Said reaction mixture also contains 0.4 weight percent (dry solids weight basis) of unreacted dextrose and 0.5 weight percent water on a total solution weight basis.

EXAMPLE 4

The ion exchange resin catalyst recovered from Example 3 above is re-used to catalyze the reaction of 800 g of n-butanol with a dextrose syrup containing about 206.5 g dextrose and 188.5 g water. The reaction apparatus, procedure and conditions as set forth in Example 3 above are again employed in this reaction.

The resulting reaction product is a n-butanol solution containing 27 weight percent solids and 1.4 weight percent water on a total solution weight basis. About 59 weight percent of the solids in said solution is the desired butyl monoglucoside and about 5 weight percent of said solids is unreacted dextrose starting material.

EXAMPLE 5

Example 2 is repeated using an aqueous D-xylose solution in place of the aqueous dextrose reactant material. Said xylose solution contains 400 g D-xylose and 200 g of water. The resulting reaction product is an n-propanol solution containing 40.5 weight percent solids (total solution weight basis), of which about 57 weight percent (dry solids weight basis) is the desired propyl monoxyloside product.

EXAMPLE 6

In this example, 168 g n-butanol; 672 g methanol; 360 g of an aqueous dextrose solution containing about 70 weight percent dextrose solids on a total solution weight basis; and 51.5 g of a commercially available macroreticular sulfonic acid ion exchange resin are charged to a glass bell reactor. The reactor is closed and its contents are heated to 115° C. with stirring over a period of about one hour. Upon reaching 115° C., the reaction mixture is maintained at that temperature, with a continued stirring, for an additional period of about 1½ hours. Upon completion of said 1½ hour reaction period an n-butanol feed stream is supplied to the reactor at a rate approximately 12 ml/minute and distillate is permitted to leave the reactor and is collected.

The indicated n-butanol addition and distillate removal is continued (while maintaining the reaction mixture at about 115° C. and providing same with continued stirring) over a period of about 3 hours with the volumetric rate of distillate removal being controlled to approximate the volumetric rate of n-butanol addition to the reaction vessel. (For the last 1 to 1¼ hour of the reaction period, a slight vacuum is maintained upon the reaction vessel to facilitate distillate removal at the desired rate). Upon completion of the foregoing, the resulting reaction mixture is permitted to cool to room temperature and is subsequently filtered to remove the ion exchange resin from the resulting n-butanol/butyl glucoside solution.

A total of 846 g of n-butanol/butyl glucoside solution is recovered from the foregoing reaction of which approximately 30 weight percent is dissolved solids. Analysis reveals that approximately 70 weight percent of said dissolved solids in butyl monoglucoside.

No phase separation is observed during the course of the above-described reaction and very little methyl glucoside products remain at the end of the stated reaction period.

While the subject matter hereof has been described and illustrated herein by reference to particular embodiments and examples thereof, such is not to be interpreted as in any way limiting the scope of the presently claimed invention.

What is claimed is:

1. A process for preparing a glycoside product by reacting a water soluble monosaccharide reactant with a $C_2$ to $C_6$ monohydric aliphatic alcohol reactant, which process comprises:
   a. admixing an aqueous solution containing, on a total aqueous solution weight basis, from about 20 to about 90 weight percent of said monosaccharide reactant with the alcohol reactant to provide a homogeneous, single phase aqueous reaction medium which comprises said monosaccharide and alcohol reactants and water and which is free of any separate and distinct aqueous phase consisting essentially of only water and the monosaccharide reactant; and
   b. reacting said monosaccharide reactant with said alcohol reactant by contacting said homogeneous aqueous reaction medium with an acid catalyst at a temperature of from about 60° to about 200° C. while removing water from the reaction mixture at a rate sufficient to prevent the formation of a separate and distinct aqueous monosaccharide solution phase during the course of said reaction.

2. the process of claim 1 wherein the alcohol reactant is a monohydric alkanol containing from 2 to 6 carbon atoms.

3. The process of claim 2 wherein the alcohol reactant is a monohydric alkanol containing from 2 to 4 carbon atoms.

4. The process of claim 1 wherein the aqueous solution of monosaccharide reactant is an aqueous glucose syrup.

5. The process of claim 4 wherein the glucose syrup contains from about 50 to about 80 weight percent glucose solids on a total syrup weight basis.

6. The process of claim 1 wherein the acid catalyst is a water soluble acid material.

7. The process of claim 6 wherein the acid catalyst is p-toluene sulfonic acid.

8. The process of claim 1 wherein the acid catalyst is a strongly acidic, solid material which is insoluble in water and in the alcohol reactant employed.

9. The process of claim 1 wherein the acid catalyst is an acidic ion exchange resin.

10. The process of claim 9 wherein the acid catalyst is a macroreticular sulfonic acid ion exchange resin.

11. The process of claim 1 wherein the reaction between said alcohol reactant and the monosaccharide reactant is conducted at a temperature of from about 80° to about 150° C.

12. The process of claim 1 wherein the alcohol reactant is selected from the group consisting of isopropanol, n-propanol, n-butanol and allyl alcohol.

13. The process of claim 1 wherein the homogeneous aqueous reaction medium is substantially saturated with the aqueous monosaccharide solution at the time that said reaction medium is contacted with said acid catalyst.

14. The process of claim 13 wherein the substantially saturated homogeneous aqueous reaction medium is obtained as a result of a countercurrent two phase liquid/liquid mass transfer process in which a dispersed discrete aqueous monosaccharide solution phase is contacted with a continuous phase of said alcohol reactant in a ratio such that the quantity of aqueous monosaccharide solution phase is in excess of that which the alcohol reactant phase is capable of dissolving and wherein the remaining, undissolved aqueous monosaccharide solution phase is separated from the resulting substantially saturated homogeneous aqueous alcohol monosaccharide reaction medium prior to contacting said reaction medium with the acid catalyst.

15. The process of claim 14 wherein the acid catalyst is a water and alcohol insoluble acidic ion exchange resin in the form of a fixed ion exchange resin bed or column through which the homogeneous aqueous alcohol monosaccharide reaction medium is passed in order to accomplish the desired alcohol monosaccharide reaction.

16. The process of claim 1 wherein the acid catalyst is a water and alcohol insoluble acidic ion exchange resin in the form of fixed ion exchange resin bed or column through which the homogeneous, aqueous alcohol/monosaccharide reaction medium is passed in order to accomplish the desired alcohol monosaccharide reaction.

17. The process of claim 1 wherein the aqueous monosaccharide solution contains, on a total aqueous solution weight basis, from about 50 to about 80 weight percent of the monosaccharide reactant.

18. The process of claim 1 wherein the alcohol reactant further comprises at least a small quantity of methanol.

19. A process for preparing glycosdes directly from an aqueous monosaccharide solution, said process comprising;
   a. admixing an aqueous solution containing, on a total aqueous solution weight basis, from about 20 to about 90 weight percent of a water soluble monosaccharide reactant with a sufficient amount of a $C_2$ to $C_6$ monohydric aliphatic alcohol reactant to completely dissolve said aqueous monosaccharide solution and to thereby provide a homogeneous, aqueous, single phase reaction medium comprising said monosaccharide and alcohol reactants and water; and
   b. contacting said homogeneous aqueous reaction medium with an acid catalyst at a temperature of from about 60° to about 200° C. to thereby cause a condensation reaction to occur between said monosaccharide and alcohol reactants to form the desired glycoside reaction product, while simultaneously removing water generated by said condensation reaction from said aqueous reaction medium at a rate sufficient to prevent the formation of a separate and distinct aqueous phase consisting essentially of only water and the monosaccharide reactant within said aqueous reaction medium.

* * * * *